(12) United States Patent
Dubow

(10) Patent No.: US 8,420,699 B1
(45) Date of Patent: *Apr. 16, 2013

(54) COMPOSITION AND METHODS OF TREATMENT USING DEIONIZED AND OZONATED SOLUTION

(76) Inventor: Irvine L. Dubow, Saint Cloud, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 13/286,213

(22) Filed: Oct. 31, 2011

Related U.S. Application Data

(63) Continuation-in-part of application No. 13/014,405, filed on Jan. 26, 2011, now Pat. No. 8,211,942, which is a continuation of application No. 10/464,105, filed on Jun. 18, 2003, now Pat. No. 7,897,642.

(60) Provisional application No. 60/389,671, filed on Jun. 19, 2002.

(51) Int. Cl.
  *A61K 47/30* (2006.01)
  *A61K 312/225* (2006.01)

(52) U.S. Cl.
  USPC .................... 514/547; 514/772.3; 514/912

(58) Field of Classification Search ............ 514/547, 514/772.3, 912
  See application file for complete search history.

(56) References Cited

U.S. PATENT DOCUMENTS

| | | |
|---|---|---|
| 2,624,756 A | 1/1953 | Bersworth |
| 2,802,788 A | 8/1957 | Flaxman |
| 3,151,084 A | 9/1964 | Schiltz et al. |
| 3,341,459 A | 9/1967 | Edison |
| 3,419,501 A | 12/1968 | Levy |
| 3,988,434 A | 10/1976 | Schole et al. |
| 4,104,187 A | 8/1978 | Sibley et al. |
| 4,116,859 A | 9/1978 | Merkl |
| 4,224,310 A | 9/1980 | Shah |
| 4,247,424 A | 1/1981 | Kuzel et al. |
| 4,279,768 A | 7/1981 | Busch |
| 4,307,109 A | 12/1981 | Arbir et al. |
| 4,357,318 A | 11/1982 | Shah et al. |
| 4,371,522 A | 2/1983 | Gilbard |
| 4,397,776 A | 8/1983 | Ward |
| 4,415,549 A | 11/1983 | Shah et al. |
| 4,422,450 A | 12/1983 | Rusteberg |
| 4,555,335 A | 11/1985 | Burris |
| 4,704,233 A | 11/1987 | Hartman et al. |
| 4,746,489 A | 5/1988 | Arnold |
| 4,775,531 A | 10/1988 | Gilbard |
| 4,847,070 A | 7/1989 | Pyrz et al. |
| 4,850,872 A | 7/1989 | Goldman et al. |
| 4,914,088 A | 4/1990 | Glonek et al. |
| 4,978,522 A | 12/1990 | Barbera et al. |
| 5,032,388 A | 7/1991 | Tikkanen |
| 5,097,556 A | 3/1992 | Engel et al. |
| 5,118,322 A | 6/1992 | Wasinger et al. |
| 5,120,460 A | 6/1992 | Asai et al. |
| 5,184,633 A | 2/1993 | Langford |
| 5,207,993 A | 5/1993 | Burris |
| 5,213,773 A | 5/1993 | Burris |
| 5,340,501 A | 8/1994 | Steindorf |
| 5,342,537 A | 8/1994 | Conville et al. |
| 5,443,801 A | 8/1995 | Langford |
| 5,449,658 A | 9/1995 | Unhoch et al. |
| 5,484,549 A | 1/1996 | Hei et al. |
| 5,496,811 A | 3/1996 | Aviv et al. |
| 5,567,444 A | 10/1996 | Hei et al. |
| 5,688,289 A | 11/1997 | Nishioka et al. |
| 5,688,516 A | 11/1997 | Raad et al. |
| 5,731,275 A | 3/1998 | Prevost et al. |
| 5,763,382 A | 6/1998 | Cooper et al. |
| 5,858,443 A | 1/1999 | Hei et al. |
| 6,076,229 A | 6/2000 | Berglund |
| 6,120,758 A | 9/2000 | Siddiqui et al. |
| 6,165,484 A | 12/2000 | Raad et al. |
| 6,267,979 B1 | 7/2001 | Raad et al. |
| 6,343,779 B1 | 2/2002 | Morita |
| 6,348,155 B1 | 2/2002 | Conway et al. |
| 6,428,453 B1 | 8/2002 | Hoppe et al. |
| 6,509,319 B1 | 1/2003 | Raad et al. |
| 6,620,797 B2 | 9/2003 | Chowhan et al. |
| 6,669,902 B1 | 12/2003 | Steiner et al. |
| 6,726,406 B2 | 4/2004 | Gilmore et al. |
| 6,875,765 B2 | 4/2005 | Knobelsdorf et al. |
| 6,953,507 B2 | 10/2005 | Kravitz et al. |
| 6,982,006 B1 | 1/2006 | Boyers et al. |
| 6,992,488 B2 | 1/2006 | Lin |
| 7,137,621 B1 | 11/2006 | Bagley |
| 7,244,354 B2 | 7/2007 | Burris et al. |
| 7,314,857 B2 | 1/2008 | Madhyastha |
| 7,425,323 B2 | 9/2008 | Schiltz |
| 7,446,089 B2 | 11/2008 | Singh et al. |
| 7,601,731 B2 | 10/2009 | Raad |
| 7,615,546 B2 | 11/2009 | Gupta |
| 7,691,283 B2 | 4/2010 | Ohba et al. |
| 7,825,079 B2 | 11/2010 | Suzuki et al. |
| 7,838,006 B2 | 11/2010 | Jirathitikal et al. |

(Continued)

OTHER PUBLICATIONS

"Infrared Spectroscopy Determination of Lead Binding to Ethylenediaminetetraacetic Acid", Journal of Chemical Education, vol. 75, No. 8, Aug. 1998, pp. 1018-1021.

(Continued)

*Primary Examiner* — Zohreh Fay
(74) *Attorney, Agent, or Firm* — Albert W. Watkins

(57) ABSTRACT

Therapeutically effective compositions and methods to inhibit dry eye as well as other conditions are provided. A therapeutically effective composition consists of at least one surfactant; a preservative with reduced immunogenicity relative to thimerosol; a complexing agent; and deionized, demineralized, ozonated water.

18 Claims, No Drawings

U.S. PATENT DOCUMENTS

| | | | |
|---|---|---|---|
| 7,879,823 | B2 | 2/2011 | Seiberg et al. |
| 7,887,679 | B2 | 2/2011 | Kitaori et al. |
| 7,897,642 | B1 | 3/2011 | Dubow |
| 7,914,799 | B2 | 3/2011 | Jira et al. |
| 7,939,488 | B2 | 5/2011 | Scheuing et al. |
| 2003/0065292 | A1 | 4/2003 | Darouiche et al. |
| 2005/0244354 | A1 | 11/2005 | Speron |
| 2006/0013845 | A1 | 1/2006 | Speron |
| 2006/0275189 | A1 | 12/2006 | Bagley |
| 2006/0275198 | A1 | 12/2006 | Bagley |
| 2007/0292355 | A1 | 12/2007 | Tamarkin et al. |
| 2008/0292498 | A1 | 11/2008 | Resch et al. |
| 2009/0114218 | A1 | 5/2009 | Veatch |
| 2009/0199874 | A1 | 8/2009 | Fletcher et al. |
| 2010/0041903 | A1 | 2/2010 | Yamazaki et al. |
| 2010/0186680 | A1 | 7/2010 | Matsumura et al. |
| 2011/0184062 | A1 | 7/2011 | Dubow |

OTHER PUBLICATIONS

Khan et al, "The effect of EDTA on the histochemical myofibrillar ATPase rection", Acta Histochem Suppl 1976:16:281-290, abstract only, 1 page, HTTP://www.ncbi.nlm.nih.gov/pubmed/154688, Oct. 10, 2011.

"Tyloxapol", HTTP://en.wikipedia.org/wiki/Tyloxapol, Jul. 7, 2011, 1 page.

"Ligand", HTTP://en.wikipedia.org/wiki/Ligand, Oct. 10, 2011, 8 pages.

"Methylparaben", HTTP://en.wikipedia.org/wiki/Methylparaben, Jul. 7, 2011, 3 pages.

"Polysorbate 80", HTTP://en.wikipedia.org/wiki/Polysorbate_80, Jul. 7, 2011, 5 pages.

"Propylparaben", HTTP://en.wikipedia.org/wiki/Propylparaben, Jul. 7, 2011, 2 pages.

"Purified water", HTTP://en.wikipedia.org/wiki/DI_water, Oct. 10, 2011, 7 pages.

Cotrait, "La structure cristalline de l'acide ethylenediamine tetraacetique, EDTA", Acta Crystallographica Section B: Structural Crystallography and Crystal Chemistry vol. 28 (3): 781, International Union of Crystallography, Mar 15, 1972, HTTP://www.deepdyve.com/Ip/international-union-of-crystallogragphy, Preview only, Oct. 10, 2011, 2 pages.

"Zwitterion", HTTP://en.wikipedia.org/w/index.php?title=Zwitterion, Oct. 10, 2011, 2 pages.

COMPOSITION AND METHODS OF TREATMENT USING DEIONIZED AND OZONATED SOLUTION

CROSS REFERENCE TO RELATED APPLICATIONS

This application is a continuation-in-part of U.S. application Ser. No. 13/014,405, filed on Jan. 26, 2011, now U.S. Pat. No. 8,211,942 which is a continuation of U.S. application Ser. No. 10/464,105, filed on Jun. 18, 2003, now U.S. Pat. No. 7,897,642 which claims the benefit of the filing date of U.S. Application Ser. No. 60/389,671, filed on Jun. 19, 2002, each naming the present inventor, the contents of each which are incorporated herein by reference in their entirety.

BACKGROUND OF THE INVENTION

1. Field of the Invention

The present invention relates to a therapeutically effective, pharmacologically acceptable, and antimicrobial composition.

2. Description of the Related Art

Many traditional therapeutic treatment solutions consist of an aqueous solution of electrolytes of low molecular weight, and may contain various carbohydrates, surfactants and synthetic polymers. Many solutions also contain a preservative with bacteriostatic or bacteriocidal properties to extend the shelf life of the solution. Unfortunately, the preservative often causes allergic reactions, some of which are severe. To address this problem, some solutions are packaged singly and without a preservative. Nevertheless, allergic reactions may also be caused by other molecules in the solution, e.g., by pathogens or other immunogenic molecules. Moreover, some solutions indiscriminately combine cations and anions as well as non-ionic agents, which renders the resulting solutions electrostatically incompatible.

Dry eye syndrome is an exemplary medical condition to which the present invention may be applied using a corresponding treatment method. A number of exemplary solutions for dry eye syndrome are illustrated in U.S. Pat. Nos. 4,371,522 by Gilbard, entitled "Keratoconjunctivitis sicca therapy"; 4,775,531 by Gilbard, entitled "Non-toxic ophthalmic preparations"; 4,914,088 by Glonek et al, entitled "Dry eye treatment solution and method"; Japanese Application 784147; and 7,897,642 by the present inventor, entitled "Compositions and methods for dry eye syndrome", the contents and teachings which are incorporated herein by reference.

Other exemplary solutions for therapeutic treatment of the eye are illustrated in U.S. Pat. Nos. 5,496,811 by Aviv et al, entitled "Submicron emulsions as ocular drug delivery vehicles"; and 6,620,797 by Chowhan et al, entitled "Artificial tear composition containing a combination of three demulcents", the contents and teachings which are incorporated herein by reference.

Other exemplary patents and published applications for various purposes, the contents and teachings of each which are incorporated herein by reference, include: U.S. Pat. No. 2,624,756 by Bersworth, entitled "Metal ion chelating compounds consisting of mono phenyl poly alkylene polyamino polycarboxylic acids and salts"; U.S. Pat. No. 2,802,788 by Flaxman, entitled "Cleaning composition for automotive cooling systems"; U.S. Pat. No. 3,151,084 by Schiltz et al, entitled "Solubilizer for synthetic detergent"; U.S. Pat. No. 3,341,459 by Edison, entitled "Detergent compositions"; U.S. Pat. No. 3,419,501 by Levy, entitled "Metal cleaning composition"; U.S. Pat. No. 3,988,434 by Schole et al, entitled "Dental preparation"; U.S. Pat. No. 4,104,187 by Sibley et al, entitled "Composition and method treating soft contact lenses at elevated temperatures"; U.S. Pat. No. 4,116,859 by Merkl, entitled "Method of preparing oxygen-containing bleach and product so produced"; U.S. Pat. No. 4,224,310 by Shah, entitled "Dentifrice compositions"; U.S. Pat. No. 4,247,424 by Kuzel et al, entitled "Stable liquid detergent compositions"; U.S. Pat. No. 4,279,768 by Busch, entitled "Service descaler for aqueous systems"; U.S. Pat. No. 4,307,109 by Arbir et al, entitled "Biocidal chelate"; U.S. Pat. No. 4,357,318 by Shah et al, entitled "Dentifrices with improved soluble fluoride availability"; U.S. Pat. No. 4,397,776 by Ward, entitled "Liquid detergent compositions containing alpha-amine oxide surfactants"; U.S. Pat. No. 4,415,549 by Shah et al, entitled "Toothpastes with reduced salinity"; U.S. Pat. No. 4,422,450 by Rusteberg, entitled "Actinic ozone periodontal irrigating apparatus and method"; U.S. Pat. No. 4,555,335 by Burris, entitled "Ozonator feed system"; U.S. Pat. No. 4,704,233 by Hartman et al, entitled "Detergent compositions containing ethylenediamine-N,N'-disuccinic acid"; U.S. Pat. No. 4,746,489 by Arnold, entitled "Method for decontaminating and cleaning ocular prostheses, particularly contact lenses, and device for implementing such method"; U.S. Pat. No. 4,847,070 by Pyrz et al, entitled "Anticalculus compositions"; U.S. Pat. No. 4,850,872 by Goldman et al, entitled "Dental restoration"; U.S. Pat. No. 4,978,522 by Barbera et al, entitled "Oral compositions"; U.S. Pat. No. 5,032,388 by Tikkanen, entitled "Method of preventing tartar formation"; U.S. Pat. No. 5,097,556 by Engel et al, entitled "Laundry waste water treatment and wash process"; U.S. Pat. No. 5,118,322 by Wasinger et al, entitled "Ozone decolorization of garments"; U.S. Pat. No. 5,120,460 by Asai et al, entitled "Dental cleaner materials"; U.S. Pat. No. 5,184,633 by Langford, entitled "Cleansing and sterilization mechanism suitable for contact lenses and the like"; U.S. Pat. No. 5,207,993 by Burris, entitled "Batch liquid purifier"; U.S. Pat. No. 5,213,773 by Burris, entitled "Treatment of liquid on demand"; U.S. Pat. No. 5,340,501 by Steindorf, entitled "Solid highly chelated warewashing detergent composition containing alkaline detersives and Aminocarboxylic acid sequestrants"; U.S. Pat. No. 5,342,537 by Conville et al, entitled "Rapid cooling system cleaning formulations"; U.S. Pat. No. 5,443,801 by Langford, entitled "Endoscope cleaner/sterilizer"; U.S. Pat. No. 5,449,658 by Unhoch et al, entitled "Biocidal compositions comprising polyhexamethylene biguanide and EDTA, and methods for treating commercial and recreational water"; U.S. Pat. No. 5,484,549 by Hei et al, entitled "Potentiated aqueous ozone cleaning composition for removal of a contaminating soil from a surface"; U.S. Pat. No. 5,567,444 by Hei et al, entitled "Potentiated aqueous ozone cleaning and sanitizing composition for removal of a contaminating soil from a surface"; U.S. Pat. No. 5,688,289 by Nishioka et al, entitled "Method of laundering clothes and textiles"; U.S. Pat. No. 5,688,516 by Raad et al, entitled "Non-glycopeptide antimicrobial agents in combination with an anticoagulant, an antithrombotic or a chelating agent, and their uses in, for example, the preparation of medical devices"; U.S. Pat. No. 5,731,275 by Prevost et al, entitled "Synergistic detergent and disinfectant combinations for decontaminating biofilm-coated surfaces"; U.S. Pat. No. 5,763,382 by Cooper et al, entitled "Cold water wash formula"; U.S. Pat. No. 5,858,443 by Hei et al, entitled "Process for effecting microbial control and reducing slime growth on hard surfaces in food processing equipment using inline ozonation"; U.S. Pat. No. 6,076,229 by Berglund, entitled "Aqueous cleaning solutions incorporating ozone-resistant surfactants with low foam characteristics"; U.S. Pat. No. 6,120,758 by Siddiqui et al, entitled "Preservative system for topically applied products"; U.S. Pat. No. 6,165,484 by Raad et al, entitled "EDTA and other chelators with or without antifungal antimicrobial agents for the prevention and treatment of fungal infections"; U.S. Pat. No. 6,267,979 by Raad et al, entitled "Chelators in combination with biocides: treatment of microbially induced biofilm and corrosion"; U.S. Pat. No. 6,343,779 by Morita, entitled "Water distribution piping of gas-dissolved cleaning water"; U.S. Pat. No. 6,348,155 by Conway et al, entitled "Water purification system and method"; U.S. Pat. No. 6,428,453 by Hoppe et al, entitled "Machine tool"; U.S. Pat. No. 6,509,319 by Raad et al, entitled "EDTA and other chelators with or without antifungal antimicrobial agents for the prevention and treatment of fungal infections"; U.S. Pat. No. 6,669,902 by Steiner et al, entitled "Ozonated foam medium and production system and method for sanitizing a food processing environment"; U.S. Pat. No. 6,726,406 by Gilmore et al, entitled "In situ formation of reactive barriers for pollution control"; U.S. Pat. No. 6,875,765 by Knobelsdorf et al, entitled "Arylsulfonamide ethers, and methods of use thereof"; U.S. Pat. No. 6,953,507 by Kravitz et al, entitled "Low temperature cleaning"; U.S. Pat. No. 6,982,006 by Boyers et al, entitled "Method and apparatus for treating a substrate with an ozone-solvent solution"; U.S. Pat. No. 6,992,488 by Lin, entitled "Self-cleaning probe system"; U.S. Pat. No. 7,137,621 by Bagley, entitled "System for super-oxygenating water"; U.S. Pat. No. 7,244,354 by Burris et al, entitled "Ozone irrigator"; U.S. Pat. No. 7,314,857 by Madhyastha, entitled "Synergistic antimicrobial compositions and methods of inhibiting biofilm formation"; U.S. Pat. No. 7,425,323 by Schiltz, entitled "Treatment and composition for achieving skin anti-aging benefits by corneum protease activation"; U.S. Pat. No. 7,446,089 by Singh et al, entitled "Methods of inhibiting and treating bacterial biofilms by metal chelators"; U.S. Pat. No. 7,601,731 by Raad, entitled "Antimicrobial flush solutions"; U.S. Pat. No. 7,615,546 by Gupta, entitled "Topical delivery system for phytosterols"; U.S. Pat. No. 7,691,283 by Ohba et al, entitled "Surfactant-based composition"; U.S. Pat. No. 7,825,079 by Suzuki et al, entitled "Cleaning composition comprising a chelant and quaternary ammonium hydroxide mixture"; U.S. Pat. No. 7,838,006 by Jirathitikal et al, entitled "Viral vaccine composition, process and methods of use"; U.S. Pat. No. 7,879,823 by Seiberg et al, entitled "Topical anti-cancer compositions and methods of use thereof"; U.S. Pat. No. 7,887,679 by Kitaori et al, entitled "Method of sterilization and electrolytic water ejecting apparatus"; U.S. Pat. No. 7,914,799 by Jira et al, entitled "Anti-fungal composition"; U.S. Pat. No. 7,939,488 by Scheuing et al, entitled "Natural disinfecting cleaners"; 2003/0065292 by Darouiche et al, entitled "Ozonated medical devices and methods of using ozone to prevent complications from indwelling medical devices"; 2005/0244354 by Speron, entitled "Oxygenated personal care products"; 2006/0013845 by Speron, entitled "Oxygenated personal care products"; 2006/0275189 by Bagley, entitled "Apparatus for generating structured ozone"; 2006/0275198 by Bagley, entitled "Method for generating structure ozone"; 2007/0292355 by Tamarkin et al, entitled "Anti-infection augmentation foamable compositions and kit and uses thereof"; 2008/0292498 by Resch et al, entitled "Disinfection System for Surfaces and Enclosed Spaces And Associated Methods"; 2009/0114218 by Veatch, entitled "Electrotherapeutic Treatment Device and Method"; 2009/0199874 by Fletcher et al, entitled "Tableware-washing process including a biocide"; 2010/0041903 by Yamazaki et al, entitled "Ozonized Surfactant"; 2010/0186680 by Matsumura et al, entitled "Livestock Sterilizing Method, Livestock Sterilizing Apparatus, and Livestock or Livestock Meat"; and 2011/0184062 by Dubow, entitled "Compositions and Methods for Dry Eye Syndrome". In addition to the foregoing, Webster's New Universal Unabridged Dictionary, Second Edition copyright 1983, is incorporated herein by reference in entirety for the definitions of words and terms used and not explicitly defined herein.

SUMMARY OF THE INVENTION

The present approach does not follow the reductionist paradigm, nor does it focus on a specific effect, such as adjusting tonicity, enhancing lubrication by augmenting and maintaining a stable tear film over the ocular surface, adding a positively or negatively charged complex of phospholipids to the ocular surface of the eye, maintaining mucin goblet cells, and the like. Instead, the present subject matter provides compositions, e.g., pharmaceutical compositions, useful in a variety of applications, wherein the components of the composition are primarily non-ionic and suitable in compositions with other components, e.g., drugs or other bioactive molecules. As used herein, a "primarily non-ionic" composition includes a composition where a majority of the components in the composition are non-ionic. In one embodiment, the composition comprises a plurality of components, the majority of which are non-ionic in nature, which results in a particularly biocompatible composition.

In one embodiment, the composition is useful to relieve eye symptoms of patients such as patients with keratoconjunctivitis sicca. For example, a composition of the invention is introduced to the ophthalmic surface of the cornea and adnexia of a patient with dry eye syndrome, e.g., a composition formulated to return the eyes and its adnexia back to their normal electrostatic adjuvant state. The solution may be used as a spray or instilled as drops. Instead of frequent instillation, the composition may be administered only once or twice a day, or as often as needed, and yet reduce or inhibit symptoms of dry eye without harmful effects. Moreover, due to the non-ionic nature of the composition, there is no allergic reaction. In one embodiment, the ophthalmic composition comprises: at least one surfactant; a component which destroys pathogens, e.g., bacteria, viruses, yeast, spores, molds, and fungi, preferably a preservative with reduced immunogenicity relative to thimerosol; a complexing agent, e.g., one which chelates metals; and deionized, demineralized, ozonated water.

In one embodiment, at least one surfactant is non-ionic. In one embodiment, at least one surfactant is present in the composition at about 0.001% to about 3.0%, e.g., about 0.01% to about 1% or about 0.02% to about 0.7%. In one embodiment, at least one surfactant is tyloxapol.

In one embodiment, the complexing agent is non-ionic. In another embodiment, the complexing agent is ionic. In one embodiment, a preferred complexing agent is EDTA. The complexing agent may be present in the composition at about 0.001% to about 3.0%, e.g., about 0.01% to about 1.0%, or about 0.02% to about 0.7%, by weight.

In one embodiment, the preservative is non-ionic. In one embodiment, the preservative may be present in the composition of about 0.01% to about 3%, e.g., about 0.1% to about 2%, by weight. In one embodiment, the preservative is parabens.

In one embodiment, the composition further comprises a fatty acid humectant. One example of a fatty acid humectant is glycerin. The fatty acid humectant is present in the composition at about 0.01% to about 3%, e.g., about 0.05% to about 2%, or 0.5% to about 1.0% by weight.

The composition may further comprise a second surfactant, e.g., Tween 80. The second surfactant is present in the composition at about 0.01% to about 3%, e.g., about 0.05% to about 1% or 0.1% to about 0.5%.

The present subject matter also provides a method of preparing a composition of the invention. The method includes combining a preservative with reduced immunogenicity relative to thimerosol, a complexing agent, at least one surfactant, and deionized, demineralized, ozonated water. In one embodiment, tyloxapol, parabens and EDTA are combined. In another embodiment, tyloxapol, parabens, EDTA, glycerin and Tween 80 are combined.

Further provided is a method to inhibit or treat dry eye syndrome. The method includes contacting an ophthalmic surface with an effective amount of a composition of the invention. In one embodiment, a composition comprises tyloxapol, parabens and EDTA and optionally a fatty acid humectant and a surfactant which is not tyloxapol.

The composition of some embodiments of the present invention may also be employed in compositions and methods to inhibit or treat other conditions, e.g., to inhibit or treat fungal infections, e.g., of the nails or skin (epidermis), as well as to improve compositions that are intended to come into contact with the skin, such as a shaving solution, or to improve cleaning solutions or products. For example, the composition of the invention can result in a shaving product that permits a smoother, closer and more comfortable shave and extends the life of razor blades. Further, the composition of one embodiment of the invention can result in a cleaning solution that, once applied, is less apt to attract dust due to its non-ionic nature.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their equivalents.

DESCRIPTION OF THE PREFERRED EMBODIMENT

In the following detailed description, specific embodiments are illustrated in which the invention may be practiced. These embodiments are described in sufficient detail to enable those skilled in the art to practice the invention, and it is to be understood that the embodiments may be combined, or that other embodiments may be utilized and that chemical, structural, logical and electrical changes may be made without departing from the spirit and scope of the present invention. The following detailed description provides examples, and the scope of the present invention is defined by the appended claims and their legal equivalents.

For the purposes of this disclosure, references to "an", "one", or "various" embodiments in this disclosure are not necessarily to the same embodiment, and such references contemplate more than one embodiment.

For the purposes of this disclosure, "a" or "an" may mean one or more. As used herein in the claim(s), when used in conjunction with the word "comprising", the words "a" or "an" may mean one or more than one. As used herein "another" may mean at least a second or more.

For the purposes of this disclosure, the phrase "therapeutically effective amount" is defined as a dosage or amount sufficient to allow the compound to perform an intended therapeutic function. The effective amounts of the compound of the invention will vary according to factors such as the degree of infection in the subject, the age, sex, and weight of the subject. Dosage regimes can be adjusted to provide the optimum therapeutic response. For example, several divided doses can be administered daily or the dose can be proportionally reduced as indicated by the therapeutic situation.

For the purposes of this disclosure, the phrase "effective amount" is defined as a dosage or amount sufficient to allow the compound to perform an intended function. In many applications of the present invention, this indicates an amount necessary to induce a killing or inhibitory effect upon microorganisms or disease-inducing matter contacted by the composition. The amount of the composition which is effective will depend upon the ingredients comprising the composition, as well as the treatment goals.

For the purposes of this disclosure, the term "pharmaceutical composition" includes preparations suitable for administration to humans. When the compounds of the present invention are administered as pharmaceuticals to humans, they can be given per se or as a pharmaceutical composition containing, for example, 0.1 to 99.5% of active ingredient in combination with a pharmaceutically acceptable carrier.

For the purposes of this disclosure, the phrases "pharmaceutically acceptable" or "pharmacologically acceptable" refer to molecular entities and compositions that do not produce an adverse, allergic or other untoward reaction when administered to a human.

For the purposes of this disclosure, the terms "pharmaceutically acceptable carrier" and "pharmaceutically acceptable buffer, solvent or diluent" include any and all fillers, diluents, solvents, dispersion media, coatings, antibacterial and antifungal agents, isotonic and absorption delaying agents and the like. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For the purposes of this disclosure, the noun "subject" includes mammals, e.g., horses, monkeys, bears, dogs, cats, mice, rabbits, cattle, squirrels, rats, and humans.

For the purposes of this disclosure, the terms "unit dose" or "dosage" refer to physically discrete units suitable for use in a subject, each unit containing a predetermined-quantity of the therapeutic composition calculated to produce the desired responses, in association with its administration, i.e., the appropriate route and treatment regimen. The quantity to be administered, both according to number of treatments and unit dose, depends on the treatment desired. Precise dosage amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance.

For the purposes of this disclosure, the phrases "a chelator" and "a complexing agent" are used interchangeably and denote one or more chelators.

For the purposes of this disclosure, the term "chelator" is defined as a molecule comprising nonmetal atoms, two or more of which atoms are capable of linking or binding with a metal ion to form a heterocyclic ring including the metal ion.

For the purposes of this disclosure, an "antimicrobial agent" is defined as an agent that has inhibitory, destructive or killing properties against bacteria, fungi, viruses and other pathogens and includes antibacterial agents, antifungal agents, antiviral agents and antiseptic agents.

For the purposes of this disclosure, the term "antibacterial agent" is defined as one or more agents having either a bactericidal or bacteriostatic effect upon bacteria contacted by the compound.

For the purposes of this disclosure, the term "bactericidal" is defined to mean having a destructive killing action upon bacteria.

For the purposes of this disclosure, the term "bacteriostatic" is defined to mean having an inhibiting action upon the growth of bacteria.

For the purposes of this disclosure, the phrase "an antifungal agent" denotes one or more antifungal agents having either a fungicidal or fungistatic effect upon fungi contacted by the compound.

For the purposes of this disclosure, the term "fungicidal" is defined to mean having a destructive killing action upon fungi.

For the purposes of this disclosure, the term "fungistatic" is defined to mean having an inhibiting action upon the growth of fungi.

For the purposes of this disclosure, the term "antiviral agent" is defined as a compound that can either kill viral agents or one that stops the replication of viruses upon contact by the compound.

For the purposes of this disclosure, the terms "contact", "contacted", "contacting", "exposed" and "exposure" are used to describe the process by which a pharmacological agent, e.g., any of the compositions disclosed in the present invention, comes in direct juxtaposition with the target cell.

For the purposes of this disclosure, the terms "mixture" and "mixing" are used in the broad sense of the words, with the term "mixing" including, but not limited to, stirring, blending, dispersing, milling, homogenizing, and other similar methods.

The composition of certain embodiments of the present invention is useful to inhibit or treat dry eye, for instance, dry eye syndrome, blepharitis, ulcerative keratitis, microcysts, microbial keratitis, conjunctivitis, hypoxia, epithelial oedema, corneal desquamation, corneal infiltrates, giant papillary conjunctivitis, keratoconjunctivitis sicca, Sjogren's syndrome and other epithelial conditions of the cornea and its adnexa, to inhibit or treat conditions of the mucous membranes of the nasal passages, oral passages and bronchi, and in other compositions due to the low immunogenicity and/or non-ionic properties of the composition, e.g., in compositions to inhibit or treat nail fungus, shaving solutions, and cleaning solutions. "Dry eye syndrome" includes one or more of the following ocular symptoms: a sandy sensation, a gritty sensation, blurriness, discomfort, foreign body sensation, burning, dryness, persistent irritation, photophobia, poor lipid dispersion with accompanying dry spots, a spotty lipid layer, and the like. There are two general categories of dry eye syndrome; one where tear secretion is insufficient (less than normal), and another where tear secretion is normal. Keratoconjunctivitis sicca (KCS) caused by Sjogren's syndrome is characterized by insufficient tear secretion and dry mouth but no definable systemic disease. Secondary Sjogren's syndrome is where there is definable systemic disease, e.g., autoimmune diseases such as rheumatoid arthritis, lupus or scleroderma. Other causes of KCS include graft versus host disease, AIDS and lymphoma involving the lacrimal glands.

The tear film has three layers. The very thin outer layer contains lipids secreted by the meibomian glands located in the lid margins and behind the eyelashes. With each blink, the oil in the glands is expressed onto the outer surface of the tear film. The primary purpose of the outer layer is to prevent evaporation of the aqueous layer of the tear film, but it also acts as a barrier to foreign body particulates. The middle (thickest) layer is the aqueous layer is secreted by the main accessory lacrimal glands. The middle layer keeps the salinity and acidity of the tears at proper levels and contains many substances the eye needs to maintain surface health and prevent infection, such as antibodies and other immune defense agents. The innermost layer is the mucin layer that is secreted by the goblet cell located on the surface of the eye. The mucin layer serves a dual purpose; it provides a protective coating for the ocular surface and is also the agent by which the aqueous layer adheres to the cornea.

An inadequate or abnormal lipid layer will, of necessity, result in an inadvertent evaporation of the aqueous tear layer, thus leaving the ocular surface susceptible to charged environmental pollutants such as dirt, dust, sand, and soilage.

Non-systemic dry eye syndrome may be caused by one or more biological or environmental factors. Those factors include the lack of oily lipid secretion, an abnormality of the oily lipid layer yielding poor and inadequate coverage of the aqueous layer, an increased osmolarity due to the decreased tear production or increased tear production, lacrimal gland disease, dysfunction of the meibomian gland, which prevents sufficient tears to stop the overflow over the edge of the lower lid, meibomitis (an infection or inflammation of the meibomian glands), a problem with the innermost mucin layer, causing a decrease in goblet cells which are vital to allow the tear film to remain on the hydrophobic epithelial layer on the surface of the cornea, stroke, close work, e.g., reading, writing, computer, side effects of certain medications, such as antibiotics, antihistamines, diuretics or anti-diuretics, hormonal changes, air conditioning, wind, dirt, dust, sand, snow, smoke, pollen, or other allergens, contact lens use, aging of the tear glands, refractive surgery, neurotrophic keratitis due to decreased corneal sensitivity or long-term contact lens wear, idiopathic and the like. The most common causes of non-systemic dry eye syndrome are the lack of oily lipid secretion, an abnormality of the oily lipid layer yielding poor and inadequate coverage of the aqueous layer, or both. Ophthalmic disorders may be detected by, for example, osmolarity measurement, dilation of the ocular surface, capillaries, arterioles and angiomas, Schirmer's test, fluorescein break-up-time, Rose Bengal staining, Lisamine Green or biomicroscope.

Such embodiments of the present subject matter disrupt the cycle of dry eyes by interrupting or breaking the cycle that causes the problem(s) and returns the ocular surface and adnexia to a normal electrostatic state. Thus, the present compositions primarily include non-ionic components, as well as any and all other substances with balancing negative and positive charged ions, so that the components in the composition complement one another. A primarily non-ionic composition comprises less than about 50% w/v or v/v, e.g., less than 10%, 1% or 0.01% w/v or v/v, of ionic components. Moreover, in one embodiment, a primarily non-ionic composition is substantially free of immunogenic agents, e.g., pathogens, which avoids the stimulation of an allergic cascade, i.e., avoids mast cell involvement and mast cell or basophil degranulation, which are major factors in the inflammatory cascade. A composition which is "substantially free" of immunogenic agents includes a composition that does not elicit an immune response or elicits an immune response that is reduced, e.g., by at least 2-fold, 10-fold or reduced by even more, relative to the immune response to one or more immunogenic agents, e.g., a pathogen, as measured by hematopoietic cell-based assays.

All allergic reactions are the result of the mobilization of the immune system in response to a foreign substance in the body. The invention is formulated to have antibodies accept the solution as friendly and non-threatening, thus avoiding an allergic cascade, even though antibodies are important as a line of defense to protect the system from harmful invading parasites, foreign bodies or pollens, and to avoid a hypersensitivity response to the eye characterized by itching, redness, tearing, foreign body sensation and decreased vision.

The process of an allergic reaction is the provocation by a specific type of antibody. Immunoglobulins, including IgE, are made by B-lymphocytes (a specific white blood cell). The B-lymphocytes antibody production is regulated/overseen by helper lymphocytes (another type of white blood cell). Macrophages (a phagocytic tissue cell), which function to protect the body against infection and noxious substances, prompt B-lymphocytes to make more IgE.

Mast cells are large cells that are comprised of basophil granules containing substances such as histamines, cytokines, and the like, which mediate allergic reactions that act on mucous glands, inflammatory cells, connective tissues, etc. Mast cells reside in the tissues of the body and basophils are in the blood stream. They both have many specific IgE antibody receptors. When the allergen (antigen) is confronted, the antigen binds to these IgE receptors on the surface of the cornea (tear film). When the IgE antibodies, next to each other, bind to the antigen, which wiggles the phospholipids membrane and causes the mast cells or basophils to degranulate, this prompts the latter to release chemicals that cause an allergic reaction.

A mast cell phospholipid membrane is composed primarily of phospholipids, carbohydrates and proteins with the phospholipids molecules arranged in parallel rows (bilayer) that consist of a polar phosphate head which is hydrophilic (water loving) facing outward and a non-polar fatty acid tail that is hydrophobic (water hating) facing inward. The membrane is the gatekeeper and acts as a barrier to control the ingress and egress into and out of the cell and organelles. There are 10 main types of lipids in cell membranes. Each type of cell or organelle generally has a differing percentage of each lipid, protein, and carbohydrate.

The membrane is relatively permeable which means some things can pass through the membrane via osmosis or diffusion. The rate of diffusion will vary depending on its: size, polarity, charge and concentration on the inside of the membrane versus the concentration on the outside of the membrane. The membrane is relatively permeable to small non-ionic molecules, particularly if they are lipid soluble and may move freely through the membrane. Macromolecules and charged ions/molecules cannot move freely through the membrane. The outside layer is positively charged and the inside layer is negatively charged. Thus, the negatively charged ions move out of the mast cells and positively charged ions move in. The permeability of the cell membrane to a molecule depends on the size of the molecule, its solubility in lipid, its ionic charge and the presence of carrier molecules.

Normal movement across the membrane is essential for nutrition and removal of waste materials. The phospholipid membrane regulates the transfer of material between the cell and its environment, it gauges the concentration gradient of adenosine triphosphate (ATP), the energy currency of the cell, and transfers the energy by varying modes: intracellular, transcellular, facilitated or passive and active transport. The lipid layer is a major barrier to a vast number of water soluble substances, e.g., proteins and carbohydrates. One role of proteins in cells is for the transport of molecules/ions into or out of cells. Other roles are in cell recognition enzyme catalysis, receptors, and in cell to cell communication. Carbohydrates repel negative particles due to their negative charge, act as receptors for hormones and other regulatory molecules, and form specific cell markers that enable like cells to attach, aggregate and enter into immune reactions.

The composition is non-ionic and the phospholipid membrane is permeable to small non-ionic molecules, thus the non-ionic molecules move freely. At first, the observation of like molecules repelling and unlike attracting, appears simple, but in fact, even though Van der Waal's forces are always present, so much depends on the charges held and under what conditions they move or whether they are at the surface or floating freely. Even though there is a motion of charges in bodies and they are electrically neutral, momentarily, at any given instant, on onset of charges may set up an electric field that reacts or disturbs to rearrange another set of charges. This changing of the electric fields that effect one another is called "Van der Waal's", "thermodynamics" or "charge fluctuation".

The formulation combines the chemical, biophysical with the biomolecular etc. It does not follow the reductionist paradigm but rather Hood's biological system. It includes intermolecular forces as, of inestimable, invaluable consideration, which may be referred to in this instance, as the Gestalt/coulomb approach, (which also includes Van der Waal forces, Debye-Huckel and London).

Coulomb's Law also known as the law of forces, is an embodiment of organic chemistry. Like Newton's Law of Gravity it too is in the same category and is scientifically fundamental. It applies to: trends in the periodic table, the relative stability of atoms and molecules, ionic vs covalent molecules, inter molecular interactions, physical properties of molecules and chemical reactivity.

According to Coulomb's law, like particles repel and unlike particles attract. The electrostatic force between two charged particles is directly proportional to the magnitude of the charge of each particle. This expansion indicates that opposite charges attract, leading to a more stable system. The converse: like charges repel and the repulsion also adds to a more stable system. This is a critical point that relates to the energy and potential energy in atoms and molecules.

Whereas Coulomb's law is relatively strong and has long range forces, the others do not. Van der Waal's forces/bonding and dispersion forces produce a temporary, fluctuating dipole action whereby the ions (electrons) are always in motion. They are the weakest of the forces, but are important because they are always present. They may be found one moment at one end of the molecule and almost instantaneously at the other end. There is constant movement of the molecules, inter and intra. This gives rise to dipole-intermolecular attraction and an instant later, both molecules reverse and in so doing will repel each other (chemguide.co.uk/atoms/bonding/vdw.html). Debye-Hunckel's Limiting law takes it one step further. This motion is not entirely random, as there is a slight tendency for the ions of the opposite charge to encounter each other frequently. The counter ions, (negative anions) have a net charge equal in magnitude but opposite in sign from the central positive cations. The atmosphere is thus ionic in nature.

The environment of the tear film lends itself greatly to this phenomenon. The aqueous component of the tear layer consists of water, electrolytes, glucose, urea, glycoproteins, primary tear proteins and serum proteins. Aqueous tears enable normal corneal metabolism since they provide the cornea with glucose, water and electrolytes. Furthermore, they provide for the elimination of carbon dioxide, lactic acid as well as flush away debris while providing lubrication of the ocular surface.

Exemplary Compositions

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The composition of various embodiments of the present subject matter may be employed in ophthalmic compositions or non-ophthalmic compositions. The ophthalmic compositions may be employed for dry eye syndrome, blepharitis, conjunctivitis, e.g., giant papillary and the like, keratitis (ulcerative or microbial), meibomitis, or in anti-bacterial ophthalmic compositions, e.g., in compositions to treat *Pseudomonas aeruginosa* infection of the eye, or any condition of the cornea, lids, orbit, glands or adnexia, eyelid and eye hygiene, and as a replacement or adjuvant for various Over-The-Counter (OTC) products. The non-ophthalmic compositions comprising one or more of the components described herein may be employed for hard surface disinfection, including for exemplary purposes, but not limited to, bathrooms, nursing homes, hospitals, homes, businesses, schools, army barracks, glass, automobiles, minors, floors, countertops, biofilms, and non-medical, medical or surgical tools. The non-ophthalmic compositions comprising one or more of the components described herein may further be employed for odor abatement and air freshening. The non-ophthalmic compositions comprising one or more of the components described herein may further be employed for fungal infections (local), e.g., fungal infection of toe nails or finger nails, or between fingers or toes (athletes foot), bacterial infections, vaginal yeast infections, and in compositions for epidermal treatment, including but not limited to lesions, abrasions, burns, cuts, infections, surgical treatment, acne, foot hygiene and infections, lotions, or to relieve external itching and irritation and other skin-associated OTC products. The non-ophthalmic compositions comprising one or more of the components described herein may further be employed for compositions administered to the bronchi, nasal passages, sinuses or for airway clearance. The non-ophthalmic compositions comprising one or more of the components described herein may further be employed as a shaving aid and cleanser. The non-ophthalmic compositions comprising one or more of the components described herein may further be employed for oral hygiene and infections, including both prophylaxis and treatment such as in dental procedures and oral sterilization as well as in general dental and oral hygiene applications and including associated OTC products. The non-ophthalmic compositions comprising one or more of the components described herein may further be employed for veterinary medicine, such as but not limited to disinfection, wound healing, etc. The non-ophthalmic compositions comprising one or more of the components described herein may further be employed for agricultural purposes, including but not limited to freshness, longevity, and safety. The non-ophthalmic compositions comprising one or more of the components described herein may further be employed for industrial purposes including metal treatment, cleaning and equipment maintenance. The non-ophthalmic compositions comprising one or more of the components described herein may further be employed for leather treatment, fabric and wood treatment, cold treatment, allergies, arthritis, digestion, autoimmune disorders, hearing treatment, blood chemistry, cancer, dementia, edema, and incorporation as a manufacturing ingredient into basic or structural materials, cosmetics, or other compounds.

The pharmaceutical compositions of the present invention may be administered by any known techniques, including parenterally and otherwise. This includes oral, nasal (via nasal spray or nasal inhaler), buccal, rectal, vaginal or topical administration. Administration may also be by orthotopic, intradermal subcutaneous, intramuscular, intraperitoneal or intravenous injection and/or infusion. Such compositions may be administered as pharmaceutically acceptable compositions that include pharmacologically acceptable carriers, buffers or other excipients. For treatment of conditions of the lungs, the preferred route is aerosol delivery to the lung. Typically, such compositions can be prepared either as liquid solutions or suspensions; solid forms suitable for use in preparing solutions or suspensions upon the addition of a liquid; and the preparations can also be emulsified.

When administration of the pharmaceutical compositions of the present invention via intravenous injection and/or infusion is the preferred route, the pharmaceutical compositions of the present invention may be administered gradually over a period of time ranging from 0.001 h to 100 h.

In one embodiment, all of the components of the composition are non-ionic, which makes the composition electrostatically quiescent biocompatible, and of low immunogenicity, i.e., which avoids or reduces inflammatory triggering mechanisms.

The composition specifically includes an aqueous vehicle that is free of an electronic charge, e.g., deionized/demineralized/non-ionized purified water. The deionized/demineralized/non-ionized purified water is subjected to ozonation to kill fungi, algae, yeast spores, microbacteria, viruses, molds and mildew, and to remove agents such as disrupted (non-intact) pathogens, prior to mixing with other substances.

For example, deionized/demineralized/non-ionic purified water is prepared by using plastic beds (exchange resins) and an advanced membrane separation technology that removes almost all the ionized mineral salts, including the salts that contribute to hardness and alkalinity. It will produce water quality that reduces 100 micro ohms to 10 micro ohms. However, as the quality of the water is very significant to the invention, the latter refers to dissolved solids only. Deionization alone does not improve or remove bacteria, viruses, fungi, microbacteria, molds, and yeast spores, etc.

One of the major benefits of ozonation is its ability to oxidize substances. While harmless, sanitary and innocuous (given Gras status by the FDA for bottled water in 1982 and generally recognized as safe in 1997), it also attenuates harmful microbes and microbial pathogen by-products. The efficacy of the composition may be monitored and the degree of effectiveness controlled. For example, ozone is most potent upon first being generated. Its half-life is 45 minutes at 68.degree. F., and in two hours its concentrated effectiveness is 16% of its initial value. It must be newly generated for immediate use in order to have the greatest lethal factor. The maximum dose is 5% ozone to 95% oxygen.

Moreover, ozonation works faster, i.e., over 3,000 times faster, than chlorine, and so is safer and more efficient and therefore a better disinfectant. Unlike chlorine, the original ozone molecule reverts back to harmless oxygen. All pathogens (algae, yeast spores, fungi, viruses, and other microorganisms) are attacked and their cell walls or outer membranes are ruptured. By reverting back to oxygen, ozone leaves no chemical residue. It is also highly reactive with synthetic products or their metabolites, as well as with their residue. It breaks down harmful chemicals and debris (such as dead microbes), which is very helpful in not triggering an inflammatory cascade. Equally important, after this action is performed, its efficacy can be controlled to the proper degree essential to perform the requisite task. In other words, the initial oxidation strength is modified as desired. Ozone can be created artificially as a result of ultraviolet light acting on oxygen, a hot spark or cold plasma.

Another component of the composition is a chelator or complexing agent, e.g., ethylene diamine tetraacetic acid trisodium salt (EDTA) or disodium edentate, EGTA, or the like. A chelate is the type of coordination compound in which a central metal ion is attached by coordinate links to two or more nonmetal atoms in the same molecule. Heterocyclic rings are thus formed during chelation, with the metal atom as part of the ring. The molecule comprising the nonmetal linking atoms is termed a chelator. The chelator or complexing agent sequesters (chelates) heavy metals such as copper, iron and nickel to form tightly bound complexes. The polyvalent metal ions form a soluble metal complex, thus improving the quality and stability of the composition. This also assists the composition to disperse metal salts and impurities to prevent deposition in the solvent and/or what may be found in lacrimal tear film. For example, EDTA is very useful to complex a metal ion, e.g., a transition metal ion that has a central cation, and optionally an attached anion or neutral molecule present in solution (or the tear layer). Thus, EDTA is a complexing agent which needs electrons and forms a very stable complex with bonds to metal ions, e.g., toxic metal ions, i.e., it sequesters metals. Suitable chelating agents can include, but are not limited to any natural or synthetic chemical which has the ability to bind divalent cationic metals.

Preferable chelators for use in the present invention include, but are not limited to, the polyacetate or polypropionate (poly)amines in the acid form or as fully or partially neutralized alkali or ammonium salts or the equivalents thereof. Some non-limiting examples include ethylenediamine-N,N,N',N'-tetraacetic acid (EDTA); the disodium, trisodium, tetrasodium, dipotassium, tripotassium, dilithium and diammonium salts of EDTA; the barium, calcium, cobalt, copper, dysprosium, europium, iron, indium, lanthanum, magnesium, manganese, nickel, samarium, strontium, and zinc chelates of EDTA; trans-1,2-diaminocyclohexane-N,N,N',N'-tetraaceticacid monohydrate; N,N-bis(2-hydroxyethyl)glycine; 1,3-diamino-2-hydroxypropane-N,N,N',N'-tetraacetic acid; 1,3-diaminopropane-N,N,N',N'-tetraacetic acid; ethylenediamine-N,N'-diacetic acid; ethylenediamine-N,N'-dipropionic acid dihydrochloride; ethylenediamine-N,N'-bis(methylenephosphonic acid) hemihydrate; N-(2-hydroxyethyl)ethylenediamine-N,N',N'-triacetic acid; ethylenediamine-N,N,N',N'-tetrakis(methylenephosphonic acid); O,O'-bis(2-aminoethyl)ethyleneglycol-N,N,N',N'-tetraacetic acid; N,N-bis(2-hydroxybenzyl)ethylenediamine-N,N-diacetic acid; 1,6-hexamethylenediamine-N,N,N',N'-tetraacetic acid; N-(2-hydroxyethyl)iminodiacetic acid; iminodiacetic acid; 1,2-diaminopropane-N,N,N',N'-tetraacetic acid; nitrilotriacetic acid; nitrilotripropionic acid; the trisodium salt of nitrilotris(methylenephosphoric acid); 7,19,30-trioxa-1,4,10,13,16,22,27,33-octaazabicyclo[11,11,11]pentatriacontane hexahydrobromide; diethylenetriamine pentaacetic acid (DTPA), and triethylenetetramine-N,N,N',N'',N''',N'''-hexaacetic acid. Suitable amino carboxylate chelating agents include ethanol-diglycines, disodium cocoyl glutamatic acid, and methyl glycine di-acetic acid (MGDA), both in their acid form, or in their alkali metal, ammonium, and substituted ammonium salt forms. Further carboxylate chelating agents for use herein include salicylic acid, aspartic acid, glutamic acid, glycine, malonic acid or mixtures and derivatives thereof. Other complexing agents include glutamic acid-N,N-diacetate ("GLDA"), and [S,S]-Ethylenediamine-disuccinic acid ("EDDS"). It is contemplated that any chelator which binds barium, calcium, cerium, cobalt, copper, iron, magnesium, manganese, nickel, strontium, or zinc will be acceptable for use in the present invention.

More preferably, the chelators for use in conjunction with the present invention may include ethylenediamine-N,N,N',N'-tetraacetic acid (EDTA); the disodium, trisodium, tetrasodium, dipotassium, tripotassium, dilithium and diammonium salts of EDTA; 1,3-diamino-2-hydroxypropane-N,N,N',N'-tetraacetic acid; 1,3-diaminopropane-N,N,N',N'-tetraacetic acid; O,O'-bis(2-aminoethyl)ethyleneglycol-N,N,N',N'-tetraacetic acid; and 7,19,30-trioxa-1,4,10,13,16,22,27,33-octaazabicyclo[11,11,11]pentatriacontane hexahydrobromide.

Most preferably, the chelators for use in the present invention may include ethylenediamine-N,N,N',N'-tetraacetic acid (EDTA) and the disodium salt of EDTA.

In one embodiment, the complexing agent is present in the composition at about 0.001% to about 5.0%, e.g., about 0.01% to about 2.5%, about 0.1% to about 2.0% or about 0.5% to about 1.0% by weight.

Another component of the composition is a non-ionic surfactant. Suitable non-ionic surfactants can include but are not limited to alkylphenol ethoxylates, alcohol ethoxylates, polyoxyethylenated polyoxypropylene glycols, polyoxyethylenated mercaptans, long-chain carboxylic acid esters, alkonolamides, tertiary acetylenic glycols, polyoxyethylenated silicones, N-alkylpyrrolidones, and alkylpolyglycosidases. Any combination of non-ionic surfactants is acceptable.

In addition to the many electronic benefits of a non-ionic surfactant discussed herein, the use of a non-ionic surfactant additionally yields significant reductions in film residue that would lead to streaking, while reducing total active ingredients in the compositions, and reducing levels of or eliminating the need for solvents, including volatile solvents such as alcohols.

Preferred non-ionic surfactants include tyloxapol and Triton X-100. For example, tyloxapol is a non-ionic alkalaryl and polyester alcohol that reduces surface tension, inhibits microscopic lipid particles in the blood stream during fat digestion and assimilation (chylomicron), and has anti-inflammatory, anti-oxidant, and mucoactive properties. In one embodiment, the non-ionic surfactant is present in the composition at about 0.001% to about 3%, e.g., about 0.05% to about 2% or about 0.1% to about 2%, about 0.01% to about 1.0% by weight.

The composition also comprises a preservative that has reduced immunogenicity relative to thimersol. The esters of p-hydrobenzoic acid are known as parabens, and include methyl, ethyl, propyl and butyl esters. Parabens is a non-ionic preservative that extends the shelf life of the composition and is very effective against yeasts and molds. In one embodiment, both methyl and propyl parabens are used in the composition, with two to three parts of methyl paraben with one part of propyl paraben. The preservative is present in the composition at about 0.01% to about 2.5%, e.g., such as about 0.5% by weight.

Other preservatives include those having the structure (I):

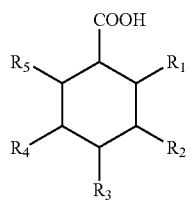

wherein $R_1$, $R_2$, $R_4$, and $R_5$ are independently selected from the group consisting of H, OH, F, I, Br, Cl, SH, $NH_2$, CN, alkyl, alkoxyl, $NR_2$, OR, $NO_2$, COR, $CONR_2$, $CO_2R$, $SO_3R$; wherein R is independently selected from the group consisting of H, alkyl, and alkoxyl groups. $R_3$ is independently selected from the group consisting H, OH, F, I, Br, Cl, SH, CN, alkyl, alkoxyl, OR, $NO_2$, COR, $CONR_2$, $CO_2R$, $SO_3R$; wherein R is independently selected from the group consisting H, alkyl, and alkoxyl groups.

Suitable alkyl groups include saturated or unsaturated, linear or branched chain, substituted or unsubstituted alkyl groups, preferably $C_1$-$C_4$, more preferably $C_1$-$C_3$, most preferably $C_1$-$C_2$ alkyl groups (preferably $CH_3$ or $CH_2C$). Non-limiting examples of substituted alkyls are $CH_2CO_2R$, $CH_2OR$, $CH_2OR$, $CH_2COR$, and $CH_2NR_2$, where R is defined as above.

Suitable alkoxyl groups include saturated or unsaturated, linear or branched chain, substituted or unsubstituted alkoxyl groups, preferably $C_1$-$C_1$, more preferably $C_1$-$C_3$, most preferably $C_1$-$C_2$ alkoxyl groups (preferably $CH_3$ or $CH_2C$).

Preferred halogens are selected from the group consisting of I, Br and Cl.

In one embodiment, the composition comprises a second non-ionic surfactant, e.g., polyoxyethylene sorbitan-mono-olleate (commercially, Tween 80), Tween 20, Tween 40, Tween 60 and Tween 85. Tween 80 promotes polymerization and acts as a wetting and penetrating agent. The effectiveness of certain surfactant combinations involving ethoxylated nonionics and semi-polar or zwitterionic surfactants such as amine oxides or sultaines, has also been recognized. The second surfactant is present in the composition at about 0.001% to about 3%, e.g., about 0.05% to about 2%, or about 0.03% to about 1%, e.g., about 0.02%, by weight.

In one embodiment, the composition comprises a humectant. Products according to the present invention in which humectant properties are desired may include amino acids, chondroitin sulfate, diglycerin, erythritol, fructose, glucose, glycerin, glycerol, glycol, 1,2,6-hexanetriol, honey, hyaluronic acid, hydrogenated honey, hydrogenated starch hydrolysate, inositol, lactitol, maltitol, maltose, mannitol, natural moisturization factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

A preferred fatty acid humectant surfactant is glycerin or glyceride derivatives (e.g., mono, di, tri, glycerides), which are fats and oils that are esters of glycerol with one or more fatty acids. These agents promote retention of moisture to prevent dehydration, and thus are moistening agents and lubricants that are resistant to oxidation. In addition, the humectant is a good emulsifier and wetting agent and will preferably also exhibit preservative or antimicrobial properties. Other humectants may include a variety of these materials can be employed and each can be present at a level of from about 0.01% to about 20%, more preferably from about 0.1% to about 10%, e.g., 0.80% or about 0.5% to about 7% by weight of the composition.

In one embodiment, the composition comprises EDTA, e.g., 0.001% to 5.0% by weight, parabens, e.g., 0.5% by weight, 2-3:1 methyl paraben to propyl paraben, tyloxapol, e.g., 0.01 to 1.0% by weight, and optionally Tween 80, e.g., 0.02% by weight, and glycerine, e.g., 0.80% by weight.

Additional formulations are suitable for oral administration. Oral formulations may include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

When the route is topical, the form may be a cream, ointment, salve or spray. For topical application, formulations may include such typical excipients as, for example, antioxidants such as acetyl cysteine, ascorbic acid, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocopherol, tocophersolan, tocopheryl acetate, tocopheryl linoleate, tocopheryl nicotinate, tocopheryl succinate, and tris(nonylphenyl)phosphite.

Where topical moisturizing properties are desired, the formulation may include acetylated lanolin, acetylated lanolin alcohol, acrylates/C10-30 alkyl acrylate crosspolymer, acrylates copolymer, alanine, algae extract, aloe barbadensis, aloe barbadensis extract, aloe barbadensis gel, althea officinalis extract, aluminum starch octenylsuccinate, aluminum stearate, apricot (prunus armeniaca) kernel oil, arginine, arginine aspartate, arnica montana extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (borago officinalis) extract, 2-bromo-2-nitropropane-1,3-diol, butcherbroom (ruscus aculeatus) extract, butylene glycol, *calendula officinalis* extract, *calendula officinalis* oil, candelilla (*euphorbia cerifera*) wax, canola oil, caprylic/capric triglyceride, cardamon (*elettaria cardamomum*) oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (anthemis nobilis) oil, cholesterol, cholesterol esters, cholesteryl hydroxystearate, citric acid, clary (salvia sclarea) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, geranium maculatum oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (lavandula angustifolia) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (prunus persica) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG-40 sorbitan peroleate, PEG-5 soy sterol, PEG-10 soy sterol, PEG-2 stearate, PEG-8 stearate, PEG-20 stearate, PEG-32 stearate, PEG-40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquarternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, shea butter (*butyrospermum parkii*), silk powder, sodium chondroitin sulfate, sodium DNA, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (glycine soja) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

Where topical ultraviolet light (UVA and UVB) absorbing properties are desired, the formulation may include benzophenone, benzophenone-1, benzophenone-2, benzophenone-3, benzophenone-4, benzophenone-5, benzophenone-6, benzophenone-7, benzophenone-8, benzophenone-9, benzophenone-10, benzophenone-11, benzophenone-12, benzyl salicylate, butyl PABA, cinnamate esters, cinoxate, DEA-methoxycinnamate, diisopropyl methyl cinnamate, ethyl dihydroxypropyl PABA, ethyl diisopropylcin namate, ethyl methoxycinnamate, ethyl PABA, ethyl urocanate, glyceryl octanoate dimethoxycinnamate, glyceryl PABA, glycol salicylate, homosalate, isoamyl p-methoxycinnamate, PABA, PABA esters, Parsol 1789, and isopropylbenzyl salicylate.

Additional skin care preparation ingredients include skin lightening agents (e.g. kojic acid, hydroquinine, ascorbic acid and derivatives, retinoids, etc.), hydroxy acids (e.g. lactic acid, salicylic acid, etc.), emollients (e.g. esters, fatty acids, etc.), vitamins (i.e. A, C, E, K, etc.), trace metals (e.g. zinc, calcium, selenium, etc.), anti-irritants (e.g. steroids, non-steroidal anti-inflammatories, etc.), antimicrobial agents (e.g.

triclosan, etc.), botanical extracts (e.g. aloe vera, chamomile, cucumber extract, ginkgo bibloba, ginseng, rosemary, etc.), dyes and color ingredients (e.g. D&C blue no. 4, D&C green is no. 5, D&C orange no. 4, D&C red no. 17, D&C red no. 33, D&C violet no. 2, D&C yellow no. 10, D&C yellow no. 11, DEA-cetyl phosphate), preservatives (e.g. BHA), emollients (i.e. organic esters, fatty acids, lanolin and its derivatives, plant and animal oils and fats, di- and triglycerides, etc.), antiirritants (i.e., steroids, nonsteroidal antiinflammatories, glycyrrhizates, etc.), antimicrobial agents (i.e., triclosan, ethanol, etc.), and fragrances (natural and artificial).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention. The scope of the invention is set forth and particularly described in the claims herein below.

I claim:

1. An antimicrobial composition consisting essentially of:
   deionized, demineralized, ozonated water;
   at least one non-ionic surfactant; and
   in combination, a preservative with reduced immunogenicity relative to thimerosol and a complexing agent, the combination in an effective amount to induce a killing or inhibitory effect upon microorganisms or disease-inducing matter contacted by the composition.

2. The composition of claim 1 further comprising a fatty acid humectant.

3. The composition of claim 2 wherein the fatty acid humectant is glycerin.

4. The composition of claim 3 which comprises about 0.5% to about 1.0% by weight glycerin.

5. The composition of claim 1 further comprising a second surfactant.

6. The composition of claim 5 wherein the second surfactant is Tween 80.

7. The composition of claim 6 which comprises about 0.05% to about 1.0% by weight Tween 80.

8. The composition of claim 1 wherein the preservative is parabens.

9. The composition of claim 8 which comprises about 0.1% to about 2% by weight paraben.

10. The composition of claim 1 wherein the complexing agent is EDTA.

11. The composition of claim 10 which comprises about 0.01% to about 1.0% by weight EDTA.

12. The composition of claim 1 wherein the at least one surfactant is tyloxapol.

13. The composition of claim 12 which comprises about 0.01% to about 1.0% by weight tyloxapol.

14. The composition of claim 1 which is primarily non-ionic.

15. The composition of claim 1 which comprises tyloxapol, parabens and EDTA.

16. The composition of claim 1 which comprises tyloxapol, parabens, EDTA, glycerin and Tween 80.

17. The composition of claim 1 which is non-ionic.

18. A topical, therapeutically effective pharmaceutical composition consisting essentially of:
    deionized, demineralized, ozonated water;
    at least one non-ionic surfactant; and
    an antimicrobial agent having a preservative with reduced immunogenicity relative to thimerosol and a complexing agent;
    the composition which comprises tyloxapol, parabens, EDTA, glycerin and Tween 80.

* * * * *